United States Patent
Drews et al.

(10) Patent No.: US 11,016,008 B2
(45) Date of Patent: May 25, 2021

(54) REAGENT NOZZLE SIPPER MIXING SYSTEM AND METHOD

(71) Applicant: Illumina, Inc., San Diego, CA (US)

(72) Inventors: Bradley Kent Drews, Poway, CA (US); Michael Dai Wang, San Diego, CA (US); Umberto Ulmanella, San Diego, CA (US); James Michael Osmus, San Diego, CA (US); Stephen Wayne Clark, San Diego, CA (US); Johanna Lynn Whitacre, San Diego, CA (US); Steven Scott Phelps, San Diego, CA (US); Michelle L. Alvarez, San Diego, CA (US); Michael Adalbert Niziolek, San Diego, CA (US); Debra Sue Bryan, San Diego, CA (US); Joshua Augustin Darland, San Diego, CA (US)

(73) Assignee: ILLUMINA, INC., San Diego, CA (US)

(*) Notice: Subject to any disclaimer, the term of this patent is extended or adjusted under 35 U.S.C. 154(b) by 575 days.

(21) Appl. No.: 15/841,098

(22) Filed: Dec. 13, 2017

(65) Prior Publication Data
US 2018/0188141 A1    Jul. 5, 2018

Related U.S. Application Data

(60) Provisional application No. 62/442,765, filed on Jan. 5, 2017.

(30) Foreign Application Priority Data

Mar. 24, 2017  (GB) ................................. 1704760

(51) Int. Cl.
*G01N 1/38* (2006.01)
*G01N 1/14* (2006.01)
(Continued)

(52) U.S. Cl.
CPC ............... *G01N 1/38* (2013.01); *B01F 3/088* (2013.01); *B01F 3/0861* (2013.01);
(Continued)

(58) Field of Classification Search
None
See application file for complete search history.

(56) References Cited

U.S. PATENT DOCUMENTS

2,588,591 A      3/1952   Thompson
2003/0086823 A1  5/2003   Fernando et al.
(Continued)

FOREIGN PATENT DOCUMENTS

EP    0005979    12/1979
EP    1138372    10/2001
(Continued)

OTHER PUBLICATIONS

GB Search Report, dated Oct. 2, 2017, in Application No. GB1704760.6.

(Continued)

*Primary Examiner* — Brian R Gordon
(74) *Attorney, Agent, or Firm* — Illumina, Inc.

(57) ABSTRACT

An analysis instrument may perform analytical operations on an analyte that is combined with multiple reagents prior to being introduced into a flow cell. The instrument may include a nozzle sipper that aspirates reagents from a recipient, along with an analyte. The reagents may be directed to a volume and may be repeatedly moved into and out of the volume by cycling of a pump. The reagents may be ejected into a destination recipient with the nozzle sipper promoting vorticity in the recipient to enhance mixing. The repeated aspiration and ejection through the nozzle sipper effectively mixes the reagents and the template in an automated or semi-automated fashion.

15 Claims, 8 Drawing Sheets

(51) Int. Cl.
*B01L 3/00* (2006.01)
*G01N 35/10* (2006.01)
*C12Q 1/6874* (2018.01)
*B01F 13/10* (2006.01)
*B01F 15/02* (2006.01)
*B01F 5/00* (2006.01)
*B01F 5/06* (2006.01)
*B01F 3/08* (2006.01)
*B01F 11/00* (2006.01)
*B01F 15/00* (2006.01)

(52) U.S. Cl.
CPC .......... *B01F 5/0065* (2013.01); *B01F 5/0647* (2013.01); *B01F 11/0074* (2013.01); *B01F 13/1055* (2013.01); *B01F 15/00876* (2013.01); *B01F 15/0243* (2013.01); *B01F 15/0283* (2013.01); *B01L 3/502* (2013.01); *B01L 3/502715* (2013.01); *B01L 3/502738* (2013.01); *B01L 3/527* (2013.01); *C12Q 1/6874* (2013.01); *G01N 35/1002* (2013.01); *G01N 35/1095* (2013.01); *G01N 35/1097* (2013.01); *B01F 2215/0037* (2013.01); *B01L 3/52* (2013.01); *B01L 2200/027* (2013.01); *B01L 2200/16* (2013.01); *B01L 2300/0832* (2013.01); *B01L 2300/0877* (2013.01); *B01L 2300/0883* (2013.01); *B01L 2400/0644* (2013.01); *G01N 35/1016* (2013.01); *G01N 2001/1418* (2013.01); *G01N 2001/1436* (2013.01); *G01N 2001/386* (2013.01); *G01N 2035/1058* (2013.01)

(56) References Cited

U.S. PATENT DOCUMENTS

| | | | | |
|---|---|---|---|---|
| 2006/0263250 | A1* | 11/2006 | Blouin | B01L 3/021 422/63 |
| 2007/0039866 | A1* | 2/2007 | Schroeder | C12Q 1/6874 210/265 |
| 2007/0202608 | A1 | 8/2007 | Uffenheimer | |
| 2013/0118900 | A1* | 5/2013 | Reimitz | B01L 3/502738 204/450 |
| 2013/0260372 | A1 | 10/2013 | Buermann et al. | |
| 2013/0316336 | A1 | 11/2013 | Matsui et al. | |
| 2015/0045234 | A1 | 2/2015 | Stone et al. | |
| 2016/0319350 | A1 | 11/2016 | Stone et al. | |

FOREIGN PATENT DOCUMENTS

| | | |
|---|---|---|
| EP | 1498736 | 1/2005 |
| JP | 03-170061 A | 7/1991 |
| WO | 93/25309 | 12/1993 |
| WO | 2006/083646 | 8/2006 |
| WO | 2011/075075 | 6/2011 |
| WO | 2012/166742 A2 | 12/2012 |

OTHER PUBLICATIONS

PCT/US2017/067836, International Search Report and Written Opinion dated Dec. 21, 2017, 13 pages.

* cited by examiner

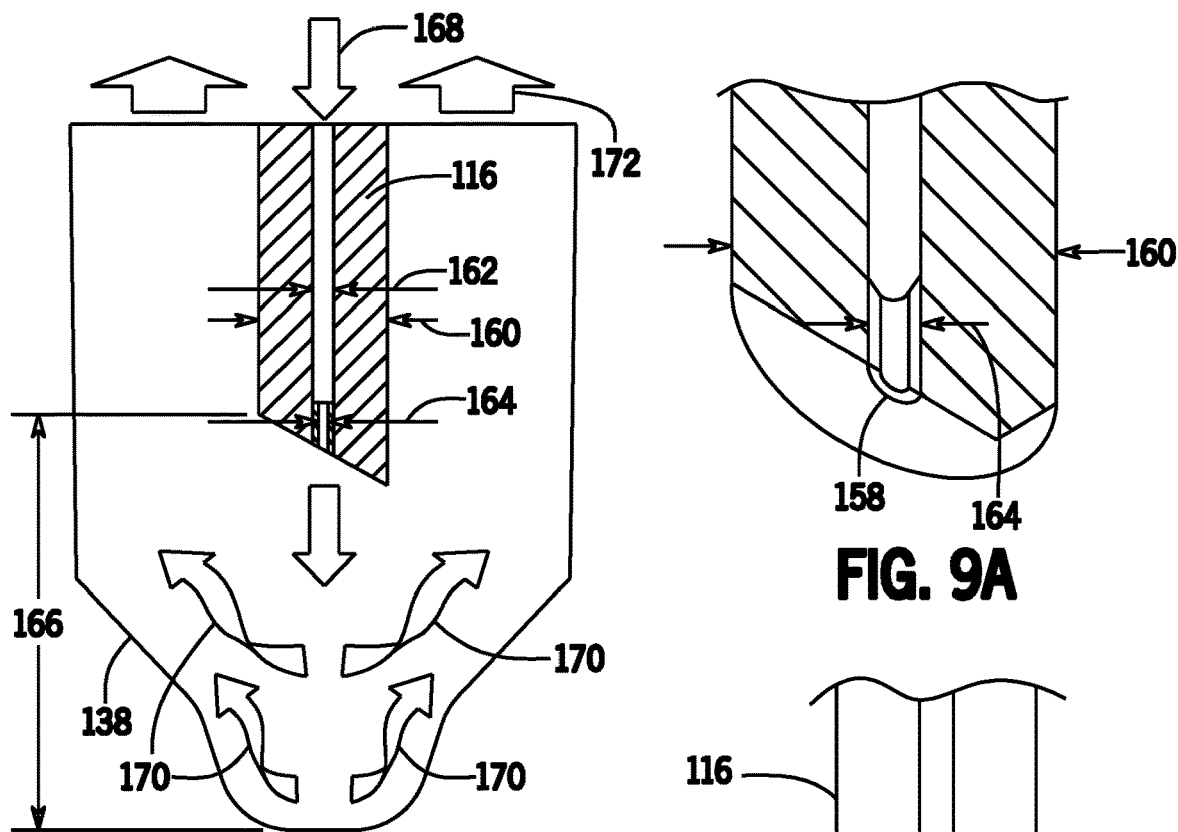
FIG. 8
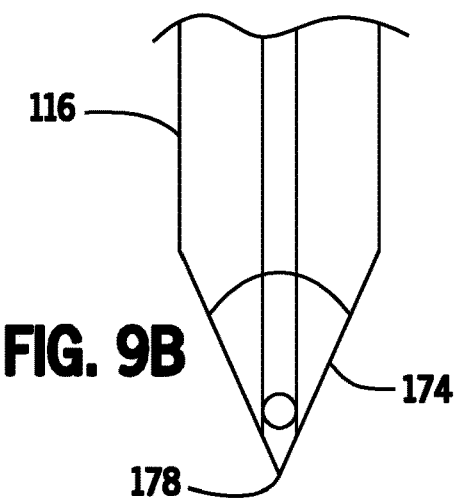
FIG. 9A
FIG. 9B
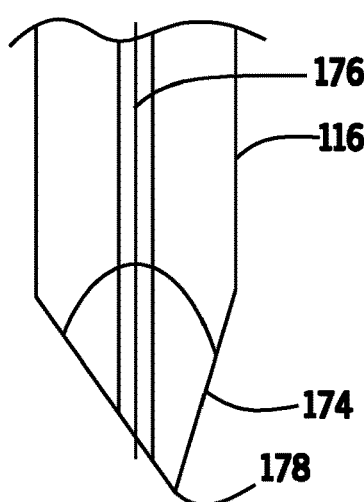
FIG. 9C
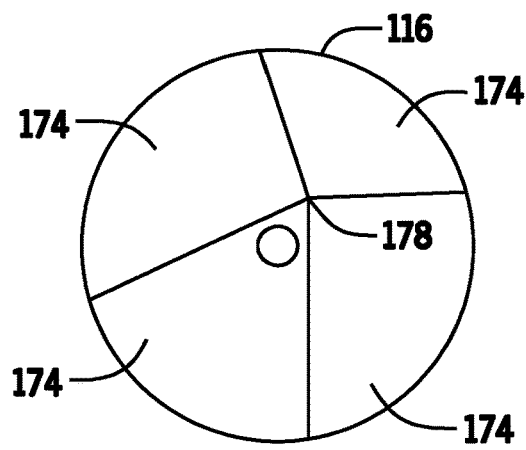
FIG. 9D

REAGENT NOZZLE SIPPER MIXING SYSTEM AND METHOD

CROSS-REFERENCE TO RELATED APPLICATIONS

This application claims benefit of priority to British (GB) Patent Application No. 1704760.6, filed Mar. 24, 2017, which claims benefit of priority to U.S. Patent Application No. 62/442,765, filed Jan. 5, 2017, as well as benefit of priority under 35 U.S.C. § 119(e) to U.S. Patent Application No. 62/442,765, filed Jan. 5, 2017, both of which are hereby incorporated by reference herein in their entireties.

BACKGROUND

Instruments have been developed and continue to evolve for sequencing molecules of interest, particularly DNA, RNA and other biological samples. In advance of sequencing operations, samples of the molecules of interest are prepared in order to form a library or template which will be mixed with reagents and ultimately introduced into a flow cell where individual molecules will attach at sites and be amplified to enhance detectability. The sequencing operation, then, includes repeating a cycle of steps to bind the molecules at the sites, tag the bound components, image the components at the sites, and process the resulting image data.

In such sequencing systems, fluidic systems (or subsystems) provide the flow of substances (e.g., the reagents) under the control of a control system, such as a programmed computer and appropriate interfaces.

SUMMARY

Details of one or more implementations of the subject matter described in this specification are set forth in the accompanying drawings and the description below. Other features, aspects, and advantages will become apparent from the description, the drawings, and the claims.

In some implementations, a system may be provided that includes a flow path to be fluidically connected with a flow cell to support analytes of interest in an analysis system; a fluidic system to aspirate reagents from reagent recipients, to mix the reagents, to eject the mixed reagents into a destination recipient, and to deliver the mixed reagents from the destination recipient to the flow path; and a nozzle sipper in fluidic communication with the fluidic system, the nozzle sipper comprising an elongated body having a central lumen extending between ends thereof and a nozzle insert disposed in a distal end of the central lumen, wherein the nozzle sipper is to both aspirate the mixed reagents from the recipient and eject mixed reagents back into the destination recipient via the nozzle insert.

In some implementations of the system, the nozzle and lumen may be dimensioned to promote vorticity mixing in the destination recipient when the reagents are expelled from the nozzle sipper through the nozzle insert and into the destination recipient.

In some implementations of the system, the lumen may have a nominal inner diameter of about 0.5 mm and the nozzle insert may be a tubular insert that has a nominal inner diameter of about 0.25 mm.

In some implementations of the system, the distal end of the nozzle sipper may have a wedged shape with facets meeting at an apex that is offset with respect to a central axis of the nozzle sipper.

In some implementations of the system, the nozzle insert may have a distal end that is shape-compliant with the wedged shape of the distal end of the nozzle sipper.

In some implementations of the system, the wedged shape may include four facets meeting at the apex.

In some implementations of the system, the nozzle sipper may extend to a nominal distance of 2 mm from a bottom surface of the destination recipient.

In some implementations of the system, the system may include a plurality of other sippers for aspirating respective reagents; the other sippers may not have nozzle inserts.

In some implementations of the system, the sipper nozzle may be to accelerate the mixed recipients to a flow velocity of at least about 1600 mm/s at a flow rate of at least about 5,000 µL/min.

In some implementations, a system by be provided that includes a flow cell to support analytes of interest in an analysis system; a fluidic system to aspirate reagents, to mix the reagents, to eject the mixed reagents into a destination recipient, and to deliver the mixed reagents from the destination recipient to the flow cell; a nozzle sipper in fluidic communication with the fluidic system, the nozzle sipper comprising an elongated body having a central lumen extending between ends thereof and a nozzle located at a distal end of the elongated body, in which the nozzle reduces a nominal interior diameter of the central lumen; and control circuitry operatively coupled to the fluidic system, the control circuitry to control the fluidic system to cause the fluidic system to: aspirate a set of the reagents one-by-one, eject the reagents in the set of reagents into the destination recipient through the nozzle, aspirate the set of reagents from the destination recipient through the nozzle for mixing, and eject the set of mixed reagents back into the destination recipient through the nozzle.

In some implementations of the system, the nozzle may include an insert inserted in the central lumen at the distal end of the nozzle sipper.

In some implementations of the system, the destination recipient may contain an analyte to be sequenced.

In some implementations of the system, the central lumen may have a nominal inner diameter of 0.5 mm and the nozzle may have a nominal inner diameter of 0.25 mm.

In some implementations of the system, the distal end of the nozzle sipper may have a wedged shape with facets meeting at an apex that is offset with respect to a central axis of the nozzle sipper.

In some such implementations of the system, the nozzle may have a distal end that is shape-compliant with the wedged shape of the distal end of the nozzle sipper.

In some implementations, a method may be provided that includes: a) actuating a pump to aspirate, one-by-one, a plurality of reagents from a corresponding plurality of reagent recipients; b) actuating the pump to eject the reagents into a destination recipient via a nozzle sipper in fluidic communication with the pump, the nozzle sipper comprising an elongated body having a central lumen extending between ends thereof and a nozzle located at a distal end of the elongated body, in which the nozzle reduces a nominal interior diameter of the central lumen; c) actuating the pump to aspirate the reagents from the destination recipient and through the nozzle sipper to further mix the reagents; and d) actuating the pump to eject the reagents from the nozzle sipper and back into the destination recipient.

In some implementations of the method, the nozzle and lumen may be dimensioned to promote vorticity mixing in the destination recipient when the reagents are expelled from the nozzle sipper through the nozzle and into the destination recipient.

In some implementations of the method, the central lumen may have a nominal inner diameter of 0.5 mm and the nozzle may include an insert that is inserted into the central lumen and that has a nominal inner diameter of 0.25 mm.

In some implementations of the method, the distal end of the nozzle sipper may have a wedged shape with facets meeting at an apex that is offset with respect to a central axis of the nozzle sipper.

In some implementations of the method, the reagents may include at least three reagents of different specific gravities.

In some implementations of the method, the method may further include performing one or more repetitions of (b) and (c) before performing (d).

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein:

FIG. 8 is a diagrammatical section of an example destination recipient vessel for mixed reagent and a sample template showing a nozzle sipper ejecting mixed reagents into the recipient;

FIGS. 9A-9D illustrate an example nozzle sipper that may be used in the mixing of the reagents;

DETAILED DESCRIPTION

Figure 1:
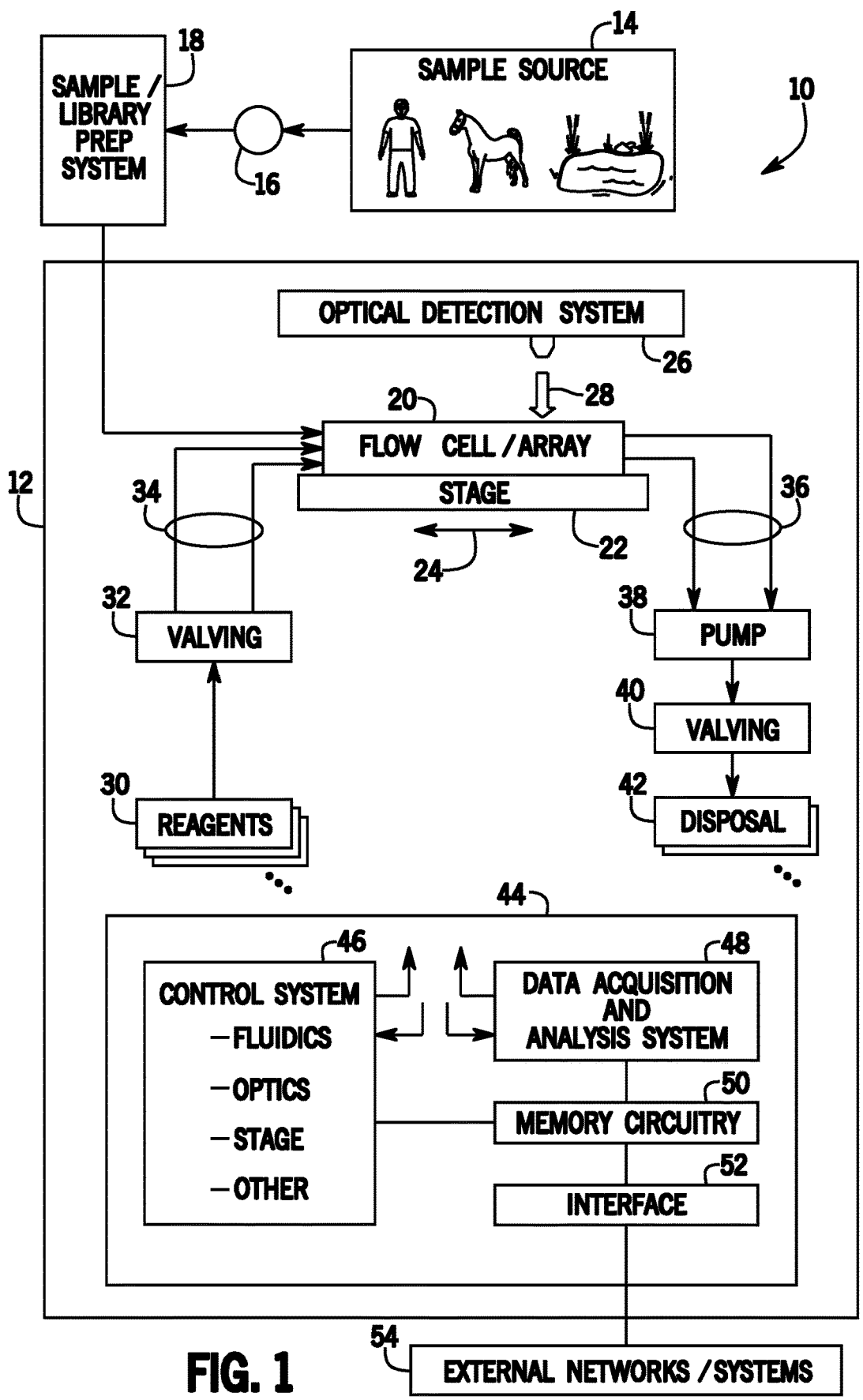
FIG. 1 is a diagrammatical overview of an example sequencing system in which the disclosed techniques may be employed.

FIG. 1 illustrates an implementation of a sequencing system 10 configured to process molecular samples that may be sequenced to determine their components, the component ordering, and generally the structure of the sample. The system includes an instrument 12 that receives and processes a biological sample. A sample source 14 provides the sample 16 which in many cases will include a tissue sample. The sample source may include, for example, an individual or subject, such as a human, animal, microorganism, plant, or other donor (including environmental samples), or any other subject that includes organic molecules of interest, the sequence of which is to be determined. The system may be used with samples other than those taken from organisms, including synthesized molecules. In many cases, the molecules will include DNA, RNA, or other molecules having base pairs the sequence of which may define genes and variants having particular functions of ultimate interest.

The sample 16 is introduced into a sample/library preparation system 18. This system may isolate, break, and otherwise prepare the sample for analysis. The resulting library includes the molecules of interest in lengths that facilitate the sequencing operation. The resulting library is then provided to the instrument 12 where the sequencing operation is performed. In practice, the library, which may sometimes be referred to as a template, is combined with reagents in an automated or semi-automated process, and then introduced to the flow cell prior to sequencing.

In the implementation illustrated in FIG. 1, the instrument includes a flow cell or array 20 that receives the sample library. The flow cell includes one or more fluidic channels that allow for sequencing chemistry to occur, including attachment of the molecules of the library, and amplification at locations or sites that can be detected during the sequencing operation. For example, the flow cell/array 20 may include sequencing templates immobilized on one or more surfaces at the locations or sites. A "flow cell" may include a patterned array, such as a microarray, a nanoarray, and so forth. In practice, the locations or sites may be disposed in a regular, repeating pattern, a complex non-repeating pattern, or in a random arrangement on one or more surfaces of a support. To enable the sequencing chemistry to occur, the flow cell also allows for introduction of substances, such as including various reagents, buffers, and other reaction media, that are used for reactions, flushing, and so forth. The substances flow through the flow cell and may contact the molecules of interest at the individual sites.

In the instrument the flow cell 20 is mounted on a movable stage 22 that, in this implementation, may be moved in one or more directions as indicated by reference numeral 24. The flow cell 20 may, for example, be provided in the form of a removable and replaceable cartridge that may interface with ports on the movable stage 22 or other components of the system in order to allow reagents and other fluids to be delivered to or from the flow cell 20. The stage is associated with an optical detection system 26 that can direct radiation or light 28 to the flow cell during sequencing. The optical detection system may employ various methods, such as fluorescence microscopy methods, for detection of the analytes disposed at the sites of the flow cell. By way of a non-limiting example, the optical detection system 26 may employ confocal line scanning to produce progressive pixilated image data that can be analyzed to locate individual sites in the flow cell and to determine the type of nucleotide that was most recently attached or bound to each site. Other suitable imaging techniques may also be employed, such as techniques in which one or more points of radiation are scanned along the sample or techniques employing "step and shoot" imaging approaches. The optical detection system 26 and the stage 22 may cooperate to maintain the flow cell and detection system in a static relationship while obtaining an area image, or, as noted, the flow cell may be scanned in any suitable mode (e.g., point scanning, line scanning, "step-and-shoot" scanning).

While many different technologies may be used for imaging, or more generally for detecting the molecules at the sites, presently contemplated implementations may make use of confocal optical imaging at wavelengths that cause excitation of fluorescent tags. The tags, excited by virtue of their absorption spectrum, return fluorescent signals by virtue of their emission spectrum. The optical detection system 26 is configured to capture such signals, to process pixelated image data at a resolution that allows for analysis of the signal-emitting sites, and to process and store the resulting image data (or data derived from it).

In a sequencing operation, cyclic operations or processes are implemented in an automated or semi-automated fashion in which reactions are promoted, such as with single nucleotides or with oligonucleotides, followed by flushing, imaging and de-blocking in preparation for a subsequent cycle. The sample library, prepared for sequencing and immobilized on the flow cell, may undergo a number of such cycles before all useful information is extracted from the library. The optical detection system may generate image data from scans of the flow cell (and its sites) during each cycle of the sequencing operation by use of electronic detection circuits (e.g., cameras or imaging electronic circuits or chips). The resulting image data may then be analyzed to locate individual sites in the image data, and to analyze and characterize the molecules present at the sites, such as by reference to a specific color or wavelength of light (a characteristic emission spectrum of a particular fluorescent tag) that is detected at a specific location, as indicated by a group or cluster of pixels in the image data at the location. In a DNA or RNA sequencing application, for example, the four common nucleotides may be represented by distinguishable fluorescence emission spectra (wavelengths or wavelength ranges of light). Each emission spectrum, then, may be assigned a value corresponding to that nucleotide. Based upon this analysis, and tracking the cyclical values determined for each site, individual nucleotides and their orders may be determined for each site. These sequences may then be further processed to assemble longer segments including genes, chromosomes, and so forth. As used in this disclosure the terms "automated" and "semi-automated" mean that the operations are performed by system programming or configuration with little or no human interaction once the operations are initiated, or once processes including the operations are initiated.

In the illustrated implementation, reagents 30 are drawn or aspirated into the flow cell through valving 32. The valving may access the reagents from recipients or vessels in which they are stored, such as through pipettes or sippers (not shown in FIG. 1). The valving 32 may allow for selection of the reagents based upon a prescribed sequence of operations performed. The valving may further receive commands for directing the reagents through flow paths 34 into the flow cell 20. Exit or effluent flow paths 36 direct the used reagents from the flow cell. In the illustrated implementation, a pump 38 serves to move the reagents through the system. The pump may also serve other useful functions, such as measuring reagents or other fluids through the system, aspirating air or other fluids, and so forth. Additional valving 40 downstream of pump 38 allows for appropriately directing the used reagent to disposal vessels or recipients 42.

The instrument further includes a range of circuitry that aids in commanding the operation of the various system components, monitoring their operation by feedback from sensors, collecting image data, and at least partially processing the image data. In the implementation illustrated in FIG. 1, a control/supervisory system 44 includes a control system 46 and a data acquisition and analysis system 48. Both systems will include one or more processors (e.g., digital processing circuits, such as microprocessors, multi-core processors, FPGA's, or any other suitable processing circuitry) and associated memory circuitry 50 (e.g., solid state memory devices, dynamic memory devices, on and/or off-board memory devices, and so forth) that may store machine-executable instructions for controlling, for example, one or more computers, processors, or other similar logical devices to provide certain functionality. Application-specific or general purpose computers may at least partially make up the control system and the data acquisition and analysis system. The control system may include, for example, circuitry configured (e.g., programmed) to process commands for fluidics, optics, stage control, and any other useful functions of the instrument. The data acquisition and analysis system 48 interfaces with the optical detection system to command movement of the optical detection system or the stage, or both, the emission of light for cyclic detection, receiving and processing of returned signals, and so forth. The instrument may also include various interfaces as indicated at reference 52, such as an operator interface that permits control and monitoring of the instrument, transfer of samples, launching of automated or semi-automated sequencing operations, generation of reports, and so forth. Finally, in the implementation of FIG. 1, external networks or systems 54 maybe coupled to and cooperate with the instrument, for example, for analysis, control, monitoring, servicing, and other operations.

It may be noted that while a single flow cell and fluidics path, and a single optical detection system are illustrated in FIG. 1, in some instruments more than one flow cell and fluidics path may be accommodated. For example, in a presently contemplated implementation, two such arrangements are provided to enhance sequencing and throughput. In practice, any number of flow cells and paths may be provided. These may make use of the same or different reagent receptacles, disposal receptacles, control systems, image analysis systems, and so forth. Where provided, the multiple fluidics systems may be individually controlled or controlled in a coordinated fashion. It is to be understood that the phrase "fluidically connected" may be used herein to describe connections between two or more components that place such components in fluidic communication with one another, much in the same manner that "electrically connected" may be used to describe an electrical connection between two or more components. The phrase "fluidically interposed" may be used, for example, to describe a particular ordering of components. For example, if component B is fluidically interposed between components A and C, then fluid flowing from component A to component C would flow through component B before reaching component C.

Figure 2:
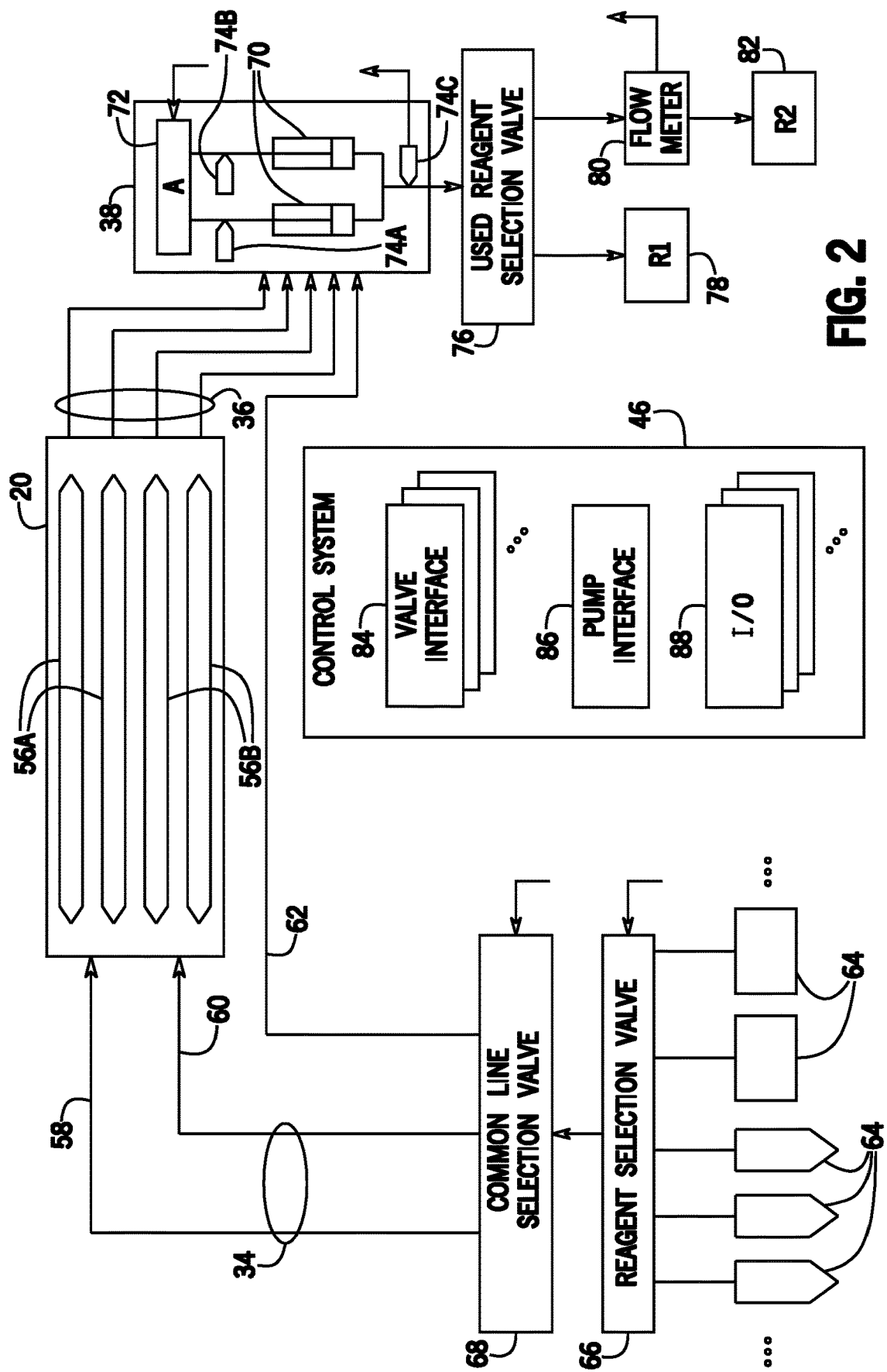
FIG. 2 is a diagrammatical overview of an example fluidic system of the sequencing system of FIG. 1.

FIG. 2 illustrates an example fluidic system of the sequencing system of FIG. 1. In the implementation illustrated, the flow cell 20 includes a series of pathways or lanes 56A and 56B which may be grouped in pairs for receiving fluid substances (e.g., reagents, buffers, reaction media) during sequencing operations. The lanes 56A are coupled to a common line 58 (a first common line), while the lanes 56B are coupled to a second common line 60. A bypass line 62 is also provided to allow fluids to bypass the flow cell without entering it. As noted above, a series of vessels or recipients 64 allow for the storage of reagents and other fluids that may be utilized during the sequencing operation.

A reagent selector valve 66 is mechanically coupled to a motor or actuator (not shown) to allow selection of one or more of the reagents to be introduced into the flow cell. Selected reagents are then advanced to a common line selector valve 68 which similarly includes a motor (not shown). The common line selector valve may be commanded to select one or more of the common lines 58 and 60, or both common lines, to cause the reagents 64 to flow to the lanes 56A and/or 56B in a controlled fashion, or the bypass line 62 to flow one or more of the reagents through the bypass line. It may be noted that other useful operations may be enabled by the bypass line, such as the ability to prime all reagents (and liquids) to the reagent selector valve (and the common line selector valve) without drawing air through the flow cell, the ability to perform washing (e.g., automated or semi-automated washing) of the reagent channels and sippers independent of the flow cell, and the ability to perform diagnostic functions (e.g., pressure and volume delivery tests) on the system.

Used reagents exit the flow cell through lines coupled between the flow cell and the pump 38. In the illustrated implementation, the pump includes a syringe pump having a pair of syringes 70 that are controlled and moved by an actuator 72 to aspirate the reagents and other fluids and to eject the reagents and fluids during different operations of the testing, verification and sequencing cycles. The pump assembly may include various other parts and components, including valving, instrumentation, actuators, and so forth (not shown). In the illustrated implementation, pressure sensors 74A and 74B sense pressure on inlet lines of the pump, while a pressure sensor 74C is provided to sense pressures output by the syringe pump.

Fluids used by the system enter a used reagent selector valve 76 from the pump. This valve allows for selection of one of multiple flow paths for used reagents and other fluids. In the illustrated implementation, a first flow path leads to a first used reagent receptacle 78, while a second flow path leads through a flow meter 80 a second used reagent receptacle 82. Depending upon the reagents used, it may be advantageous to collect the reagents, or certain of the reagents in separate vessels for disposal, and the used reagent selector valve 76 allows for such control.

It should be noted that valving within the pump assembly may allow for various fluids, including reagents, solvents, cleaners, air, and so forth to be aspirated by the pump and injected or circulated through one or more of the common lines, the bypass line, and the flow cell. Moreover, as noted above, in a presently contemplated implementation, two parallel implementations of the fluidics system shown in FIG. 2 are provided under common control. Each of the fluidics systems may be part of a single sequencing instrument, and may carry out functions including sequencing operations on different flow cells and sample libraries in parallel.

The fluidics system operates under the command of control system 46 which implements prescribed protocols for testing, verification, sequencing, and so forth. The prescribed protocols will be established in advance and include a series of events or operations for activities such as aspirating reagents, aspirating air, aspirating other fluids, ejecting such reagents, air and fluids, and so forth. The protocols will allow for coordination of such fluidic operations with other operations of the instrument, such as reactions occurring in the flow cell, imaging of the flow cell and its sites, and so forth. In the illustrated implementation, the control system 46 employs one or more valve interfaces 84 which are configured to provide command signals for the valves, as well as a pump interface 86 configured to command operation of the pump actuator. Various input/output circuits 88 may also be provided for receiving feedback and processing such feedback, such as from the pressure sensors 74A-C and flow meter 80.

Figure 3:
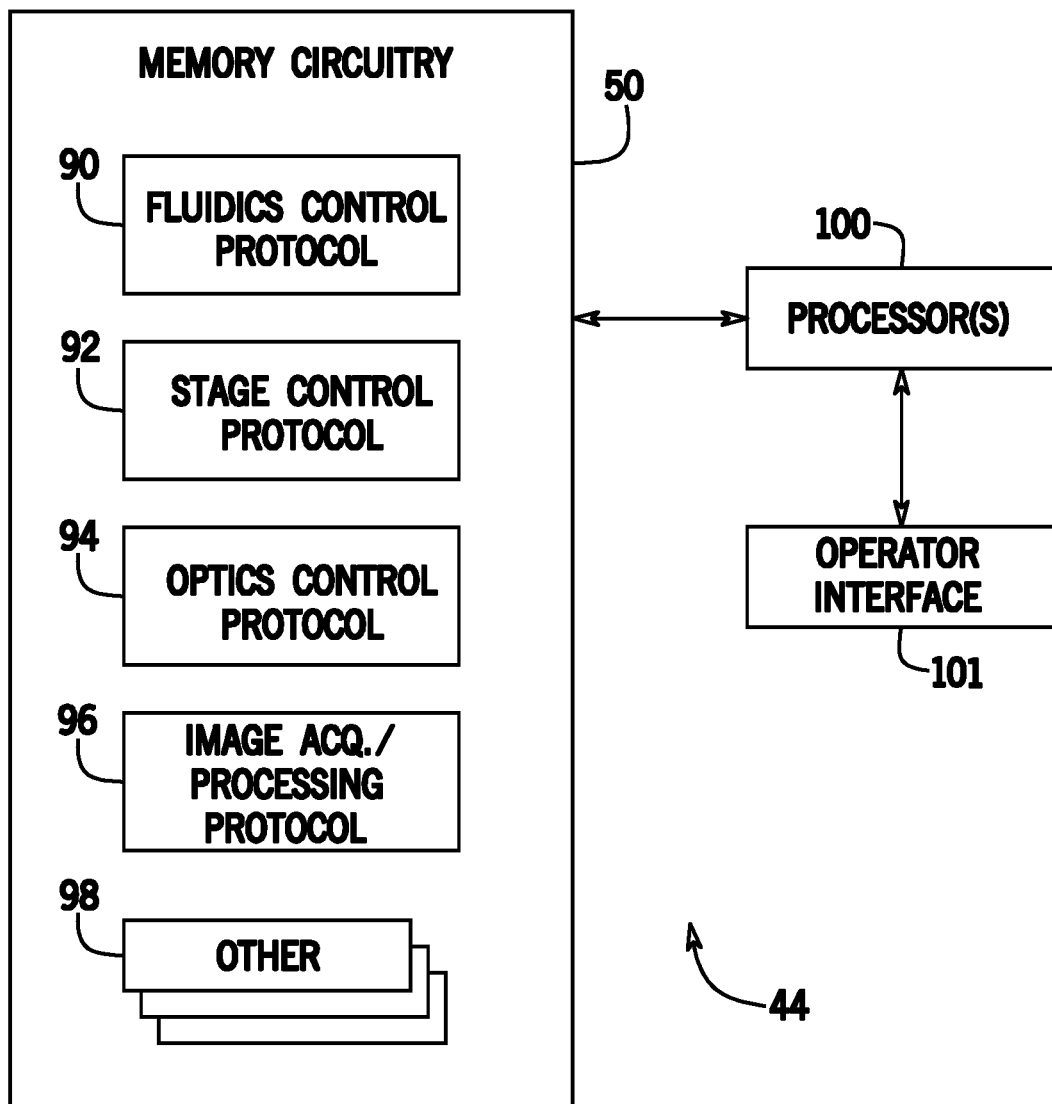
FIG. 3 is a diagrammatical overview of an example processing and control system of the sequencing system of FIG. 1.

FIG. 3 illustrates certain functional components of the control/supervisory system 44. As illustrated, the memory circuitry 50 stores prescribed routines that are executed during testing, commissioning, troubleshooting, servicing, and sequencing operations. Many such protocols and routines may be implemented and stored in the memory circuitry, and these may be updated or altered from time to time. As illustrated in FIG. 3, these may include a fluidics control protocol 90 for controlling the various valves, pumps, and any other fluidics actuators, as well as for receiving and processing feedback from fluidics sensors, such as valves, and flow and pressure sensors. A stage control protocol 92 allows for moving the flow cell as desired, such as during imaging. An optics control protocol 94 allows for commands to be issued to the imaging components to illuminate portions of the flow cell and to receive returned signals for processing. An image acquisition and processing protocol 96 allows for the image data to be at least partially processed for extraction of useful data for sequencing. Other protocols and routines may be provided in the same or different memory circuitry as indicated by reference 98. In practice, the memory circuitry may be provided as one or more memory devices, such as both volatile and non-volatile memories. This memory may be within the instrument, and some may be off-board.

One or more processors 100 access the stored protocols and implement them on the instrument. As noted above, the processing circuitry may be part of application-specific computers, general-purpose computers, or any suitable hardware, firmware and software platform. The processors and the operation of the instrument may be commanded by human operators via an operator interface 101. The operator interface may allow for testing, commissioning, troubleshooting, and servicing, as well as for reporting any issues that may arise in the instrument. The operator interface may also allow for launching and monitoring sequencing operations.

Figure 4:
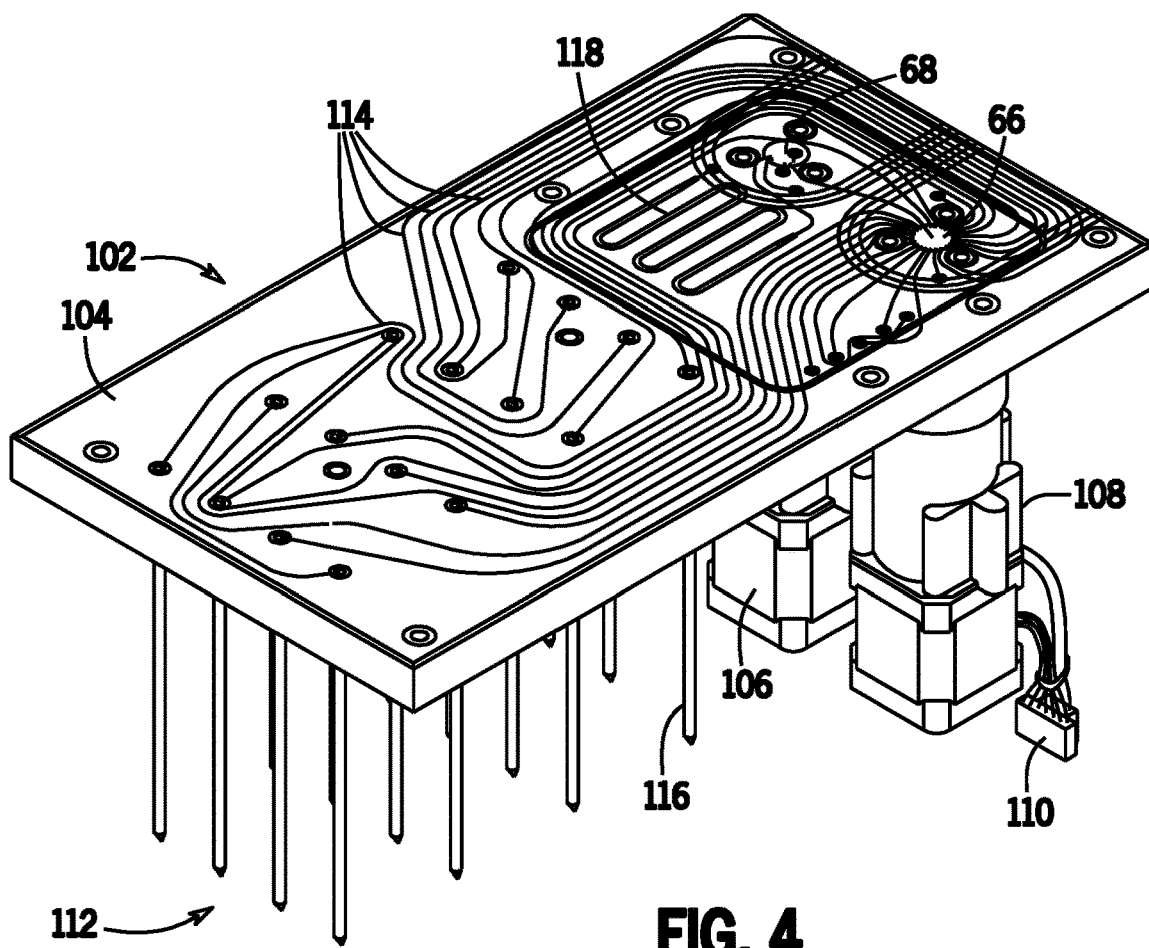
FIG. 4 is a perspective view of an example of a reagent manifold with selector valves.

FIG. 4 illustrates a valve assembly that serves to draw reagents and other fluids from recipients and deliver them to the flow cell. The valve assembly 102 includes a manifold structure 104 in which channels are formed to define flow paths for the reagents and other fluids. As can be seen in FIG. 4, the valves 66 and 68 are driven and controlled by motors 106 and 108. One or more motor interfaces or connections 110 provide power and, where desired, signals to and from the motors. As noted above, the motors (and thereby the valves) are controlled by the control circuitry during testing, commissioning, and servicing, as well as during the sequencing operation.

The reagent and fluid pathways within the manifold are coupled to sippers 112 that, during operation, draw reagents and other fluids from respective recipients (not shown). The flow paths for the reagents and fluids, designated generally by reference 114 in FIG. 4, may be formed by molding, etching, or any other suitable process to allow the reagents and fluids to move from the sippers to the valves when the pump discussed above is commanded to aspirate the reagents and fluids. At least one of the sippers is configured as a nozzle sipper 116 to assist in mixing of reagents during the sequencing operation (e.g., prior to reactions and imaging). Also illustrated in FIG. 4 is a mixing volume configured as a channel 118 in which reagents and fluids can be drawn and moved for mixing. In some implementations, the mixing volume may be a portion or all of the bypass line 62. For example, reagents may be aspirated into the bypass line 62 in a desired sequence but such that the reagents do not traverse the entire length of the bypass line (which may cause them to be routed to disposal). Once the bypass line (or a portion thereof serving as the mixing volume) has been loaded with the desired sequence of reagents, the end of the bypass line through which the reagents were introduced may be switched, using a valve, so as to fluidically connect with a flow path leading to, for example, a destination recipient so that the entire set of reagents loaded into the bypass line may then be expelled back out of the bypass line and into the destination recipient. In other implementations, the mixing volume may, for example, be a destination recipient, e.g., the destination recipient from to which the pre-mixed fluids are delivered, or a separate destination recipient, e.g., one that is completely empty prior to delivery of the selected reagents.

Figure 5:
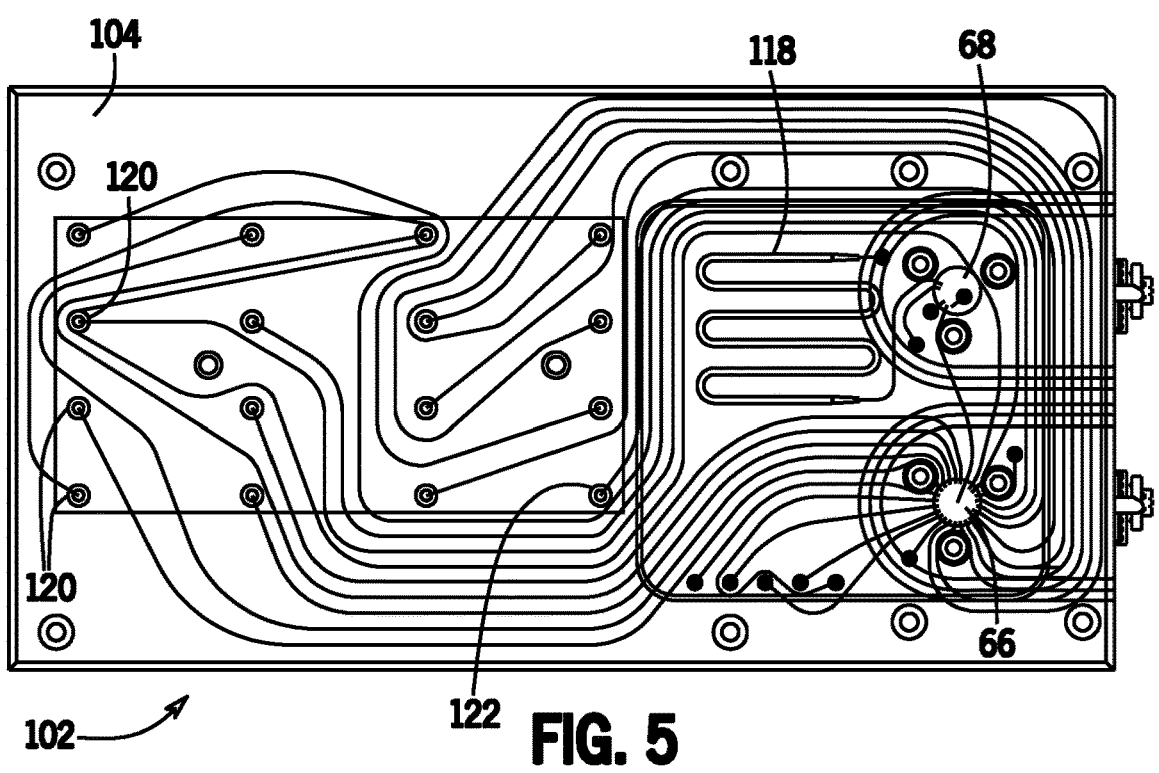
FIG. 5 is a top view of the example manifold and valve arrangement of FIG. 4.

FIG. 5 is a top view of the valve assembly 102. Here again, the valves 66 and 68 are visible in the manifold and coupled to the flow paths for the reagents and fluids. The reagent selector valve 66 receives the reagents from the sippers, and directs the aspirated fluids to the common line selector valve 68. The mixing channel 118 is coupled to the common line selector valve to allow for mixing of reagents as described below. Also shown in FIG. 5 are ports 120 provided in the manifold to allow for coupling the manifold to the sippers. One of the ports 120 (indicated by reference 122) will be coupled to the nozzle sipper to allow for injection of reagents into a destination recipient, and for drawing the reagents from the destination recipient for mixing. The destination recipient, for example, may be a container, tube, or other vessel designed to contain the reagents. The destination recipient may, for example, be used as a temporary work volume to which reagents and/or other materials may be transferred in order to prepare them for delivery, e.g., by mixing, to the flow cell. Thus, reagents and other fluids may, once prepared in the destination recipient, be transferred from the destination recipient to the flow cells.

Figure 6A:
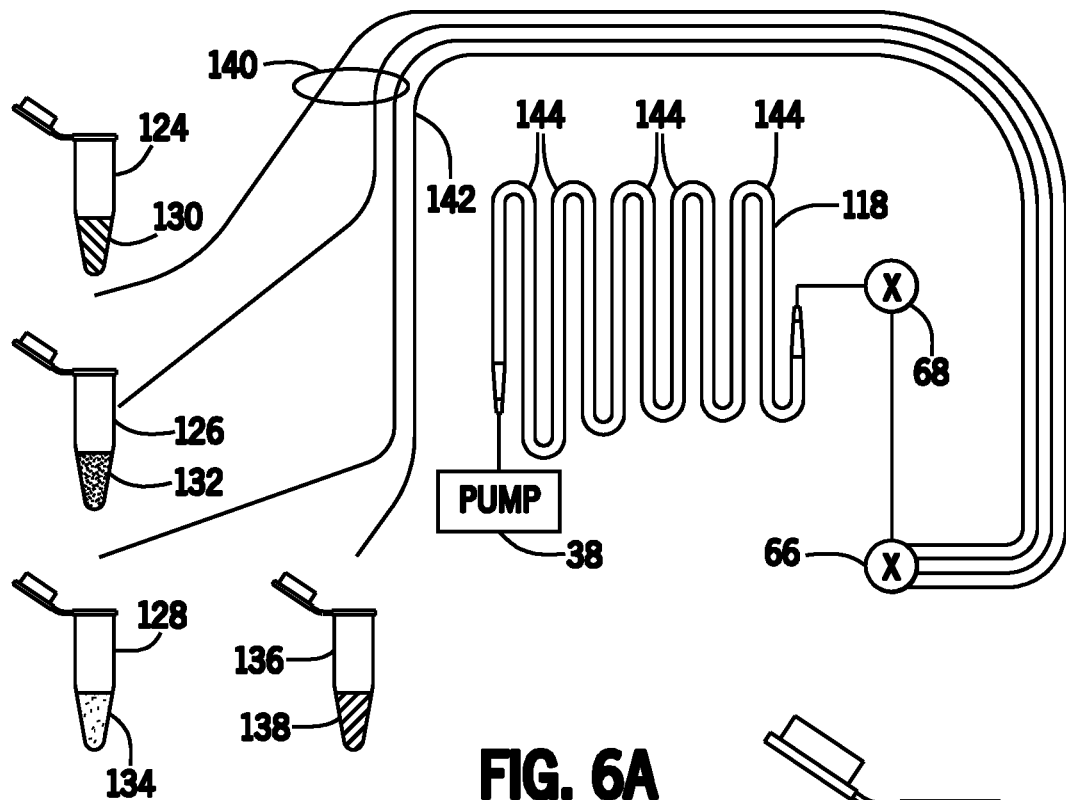
FIG. 6A is a diagrammatical view of an example arrangement for aspirating and mixing reagents and a sample template, while FIG. 6B show how reagents and a sample template would be striated prior to mixing.

A presently contemplated implementation of the mixing channel 118 and reagent flow paths for mixing is illustrated in FIG. 6A. As noted above, the mixing channel 118 is coupled to the common line selector valve 68, which in turn is coupled to an outlet of the reagent selector valve 66. The mixing channel 118 is also coupled to the pump 38 to allow for aspiration and ejection of reagents and fluids as described below. In the implementation illustrated in FIG. 6A, reagent recipient or vessels 124, 126, and 128 store reagents 130, 132, and 134, respectively. A further or destination recipient 136 stores, in this example, a pre-prepared sample template or library 138. For the mixing operation the reagents 130, 132 and 134 are pre-mixed and then combined with the template 138. To allow such pre-mixing, the reagents are aspirated one-by-one into the mixing channel 118 through respective flow paths indicated in FIG. 6A by reference 140. A further flow path 142 allows the reagents to be deposited in the destination recipient 136 along with the template. In the illustrated implementation, the mixing channel 118 forms a serpentine internal volume having loops 144 that allow for the desired volumes of reagents to be aspirated and mixed in a relatively compact area of the manifold.

Figure 6B:
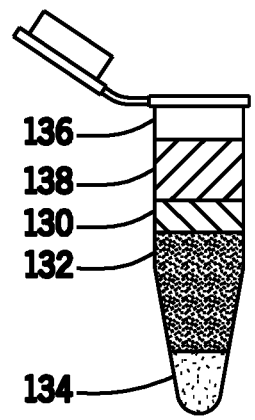

In a presently contemplated implementation, the reagents 130, 132, and 134 have different fluid properties that pose challenges to the mixing. For example, the densities of the reagents differ, and substantial differences may exist between the viscosities and oil interfacial tensions of the reagents. In a presently contemplated implementation, for example, the viscosities vary between approximately 1.5 cP and 50 cP, e.g., 2.4 cP at 25° C., while oil interfacial tensions vary between about 5.0 and about 19.2 dynes/cm. The template, by comparison, may have a still different density and a lower viscosity (e.g., on the order of 1 cP at 25° C.) and a different oil interfacial tension (e.g., on the order of about 9.8 dynes/cm). FIG. 6B illustrates striation of the reagents and template in the destination recipient 136 when not mixed. In the illustrated implementation, the template comprises about 30% of the total volume, while reagent 130 comprises about 22%, reagent 132 comprises about 42%, and reagent 134 comprises about 6%. In the present context, the term "about" is intended to mean that the values indicated are not exact and the actual value may vary from those indicated in a manner that does not materially alter the operation concerned.

Figure 7:
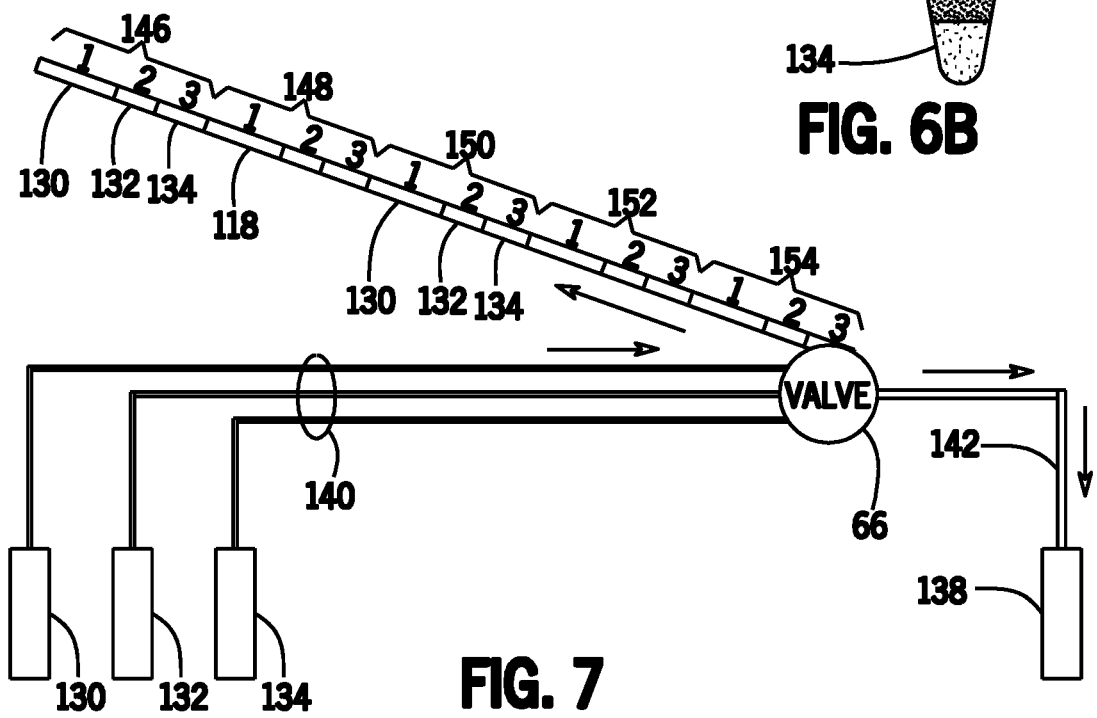
FIG. 7 is a diagrammatical view of an example of how reagents to be mixed may be aspirated individually into a mixing volume.

To permit automated mixing of the reagents and template, the fluidics system and its control allow for the reagents to be selectively aspirated one-by-one into the mixing channel, injected into the destination recipient, and cyclically withdrawn and re-injected for mixing. FIG. 7 illustrates a presently contemplated technique for the reagent aspiration. As shown, the reagents 130, 132, and 134 are aspirated one-by-one by control of valve 66. With the common line selector valve directing the reagents to the mixing channel, several sets of volumes of each reagent are aspirated as indicated by reference numerals 146, 148, 150, 152, and 154. To provide for reduction of pressure spikes during mixing, the pump may also aspirate a volume of air prior to aspirating the reagents. The air volume provides a cushion that limits positive and negative pressure spikes during mixing. In the implementation illustrated in FIG. 7, the aspirated air would be located to the upper left of the reagent sets. Moreover, a liquid buffer may be aspirated that aids in priming, washing, and pushing the reagents. Once aspirated as illustrated in FIG. 7, the valving can be then controlled to allow the pump to inject the reagents into the template 138 which will be pre-loaded into the template recipient 136 described above.

In another technique in which three or more reagents may be selected for mixing in the destination recipient, at least two of the reagents selected for mixing may be repeatedly introduced one-by-one into the mixing channel, with at least one other reagent selected for mixing being held in reserve until the reagents that are repeatedly introduced one-by-one to the mixing channel have been fully delivered to the mixing channel. The reserved reagent may then be added all at once to the mixing channel. For example, if reagents A and B are to be repeatedly introduced one-by-one into the mixing channel, followed by reserved reagent C, then the reagents in the mixing channel would generally be layered as ABABABABABC, as opposed to ABCABCABCAB-CABC (which would result from, for example, a technique similar to that discussed with respect to FIG. 7). Such a technique is believed to be advantageous in preventing or reducing the occurrence of, for some reagents, undesired reaction byproducts. For example, the reserved reagent may react with one of the other reagents in isolation in one particular manner, but may react with two or more of the other reagents in combination in another manner. The latter may be the desired reaction that may occur once the reagents have been thoroughly mixed, whereas the former may occur during pre-mixing when the reagents may still be relatively stratified and may only mix with the directly adjacent neighboring reagent. In another example, the reserved reagent may react with the material that forms the structure of the mixing channel and produce an undesired byproduct. Since the repeated one-by-one introduction of reagents to the mixing channel may require several minutes, e.g., 5 minutes, 10 minutes, 15 minutes, or longer, depending on the number and quantity of each reagent desired, reserving the introduction of potentially troublesome reagents until after the other reagents have been delivered one-by-one to the mixing channel may significantly reduce the amount of time that the reserved reagent spends in contact with the other reagents and with the structure of the mixing channel, thereby reducing the potential for undesirable reaction byproducts to be generated. Of course, in such implementations, the reserved reagent may not benefit from the pre-mixing that the other reagents benefit from, but the reduced potential for undesirable reaction byproducts may outweigh the loss of the pre-mixing with respect to the reserved reagent. In particular, if the reserved reagent is a lower-viscosity liquid, the loss of pre-mixing with respect to the reserved agent may ultimately have little impact.

The use of a channel-like mixing volume, e.g., a volume that is much longer in length than it is wide (for example, at least 10×, 100×, 150× to 170×, 160×, 200×, or 500× longer than it is wide) may allow the serially-delivered reagents to maintain a relatively stratified arrangement relative to one another within the channel by reducing the surface-to-surface contact interface area between each layer of reagents (the reagents are liquid and will thus likely diffuse into each other across this boundary to some extent over time, so the boundary/contact interface areas referenced herein are to be understood to be theoretical in nature; reducing these theoretical areas will, however, slow the rate of diffusion). In addition, for reagents that may be somewhat immiscible with one another, a mixing volume that is, for example, spherical in shape or that has a larger width-to-length ratio may allow the various reagent doses that are delivered into the mixing volume to float within the mixing volume and potentially re-combine with earlier doses of that same reagent, thereby losing the stratification that may be achieved in a channel-like mixing volume. For example, a mixing channel that is approximately 2.25 mm in diameter or width for approximately 360 mm of its length may provide advantageous stratification in delivered reagents during the pre-mixing process. Once the mixing volume has been loaded with the desired quantities of the multiple sets of reagents, the contents of the mixing volume may be delivered to the destination recipient (some portion of the fluids in the mixing volume may be lost to the dead volume of the fluidic system; the total volume of the reagents delivered to the mixing volume may be calibrated to account for such loss). After delivery to the destination recipient, the delivered pre-mixed reagents may be repeatedly aspirated from and ejected back into the destination recipient to promote further mixing. In some implementations, the pre-mixed (or post-pre-mixed) reagents may be aspirated from the destination recipient and pulled back into the mixing volume before being ejected back into the destination recipient. Thus, in such implementations, the pre-mixed reagents may be moved into and out of the mixing volume repeatedly during the aspiration/ejection mixing operation.

It has been found that the use of the mixing channel with a nozzle sipper that promotes vorticity in the destination recipient and provides excellent mixing of reagents and the template despite substantial differences in fluid properties of the reagents. Moreover, these structures and techniques enable automated mixing with little or no human interaction. An example nozzle sipper for use in these techniques is illustrated an FIGS. 8 and 9A-9C. As shown in FIG. 8, the nozzle sipper has an elongated body with a central lumen (cavity) extending along its length and a tip 156 at its distal end. A nozzle is provided at the tip to reduce the inner diameter of the sipper at this location to increase the velocity of fluids aspirated and ejected through the sipper. In the illustrated implementation, the nozzle is formed as an insert 158 that is lodged in the distal end or tip of the sipper. Other structures, such as caps, machined, formed, upset regions, and so forth could form the nozzle.

In the illustrated implementation, the sipper as a nominal outer diameter 160 of about 0.125 inches (3.175 mm), and a nominal inner diameter 162 of 0.020 inches±0.001 inches (0.508 mm). The nozzle, on the other hand, as a nominal inner diameter 164 of 0.010 inches±0.001 inches (0.254 mm, although some implementations may feature a nozzle inner diameter ranging up to between 0.20 and 0.28 mm). Of course, other sizes and dimensions may be utilized to provide the desired mixing. Further, in the illustrated implementation, the nozzle sipper 116 is positioned at a height 166 above the bottom of the recipient 138 of approximately 2 mm. As the reagents are injected into the recipient, then, as indicated by reference 168, vorticity within the recipient is enhanced by virtue of the increased velocity of the reagents moving through the nozzle, thereby enhancing mixing in the recipient, as indicated by arrows 170 in FIG. 8. The mixed reagents are allowed to rise in the recipient as indicated by reference 172.

FIG. 9A illustrates the distal end of the nozzle sipper in somewhat greater detail. As can be seen in the figure, the nominal inner diameter 162 of the sipper is reduced by the nozzle insert 158, in this case to approximately one half of the inner diameter of the sipper (the nozzle insert, in this example, is tubular in shape). A presently contemplated form of the distal end is best illustrated in FIGS. 9B, 9C and 9D. As shown here, the nozzle sipper has a faceted lower extremity comprising four facets 174, giving the appearance of a wedged shape to the nozzle sipper tip. The sipper has a centerline 176, and the facets meet in an apex 178 that is offset or eccentric with respect to the centerline 176. This geometry of the distal end reduces or avoids dragging or scraping of the recipient as the sipper is lowered into the recipient, or as the recipient is raised around the sipper. It may be noted, however, that in the illustrated implementation, the insert has a lower contour that matches the contour of the tip (e.g., one or more of the angled facets). Put another way, the insert may be shape-compliant with the faceted or the wedged shape of the distal end of the nozzle sipper. Moreover, it may be noted that in a presently contemplated implementation the sipper and nozzle are made of an engineering plastic, such as polyetheretherketone (PEEK). Such materials may provide chemical resistance to the reagents and any solvents used in the process.

Figure 10:
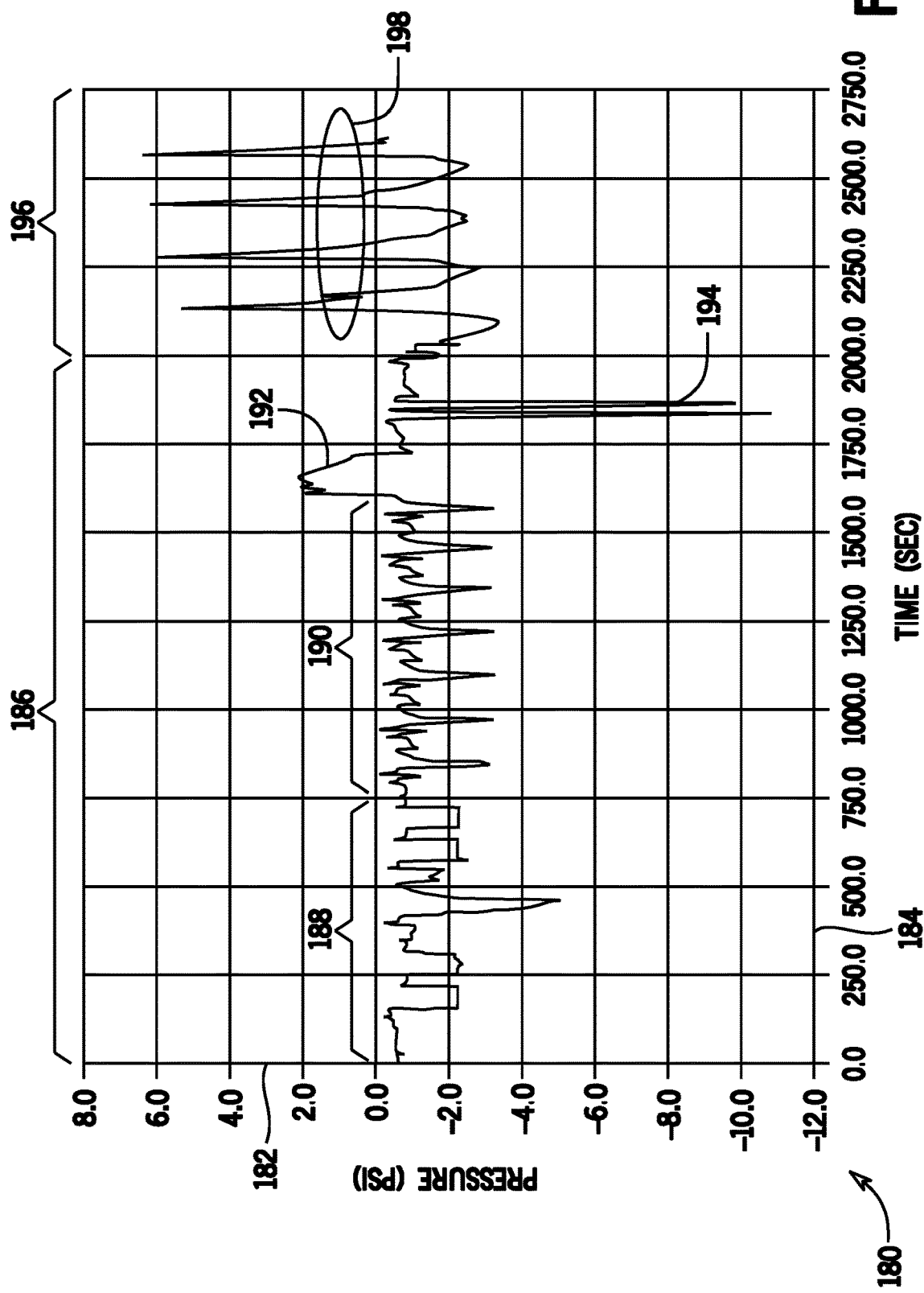
FIG. 10 is a graphical representation of example cycles in aspirating and mixing reagents and a sample template.
Figure 11:
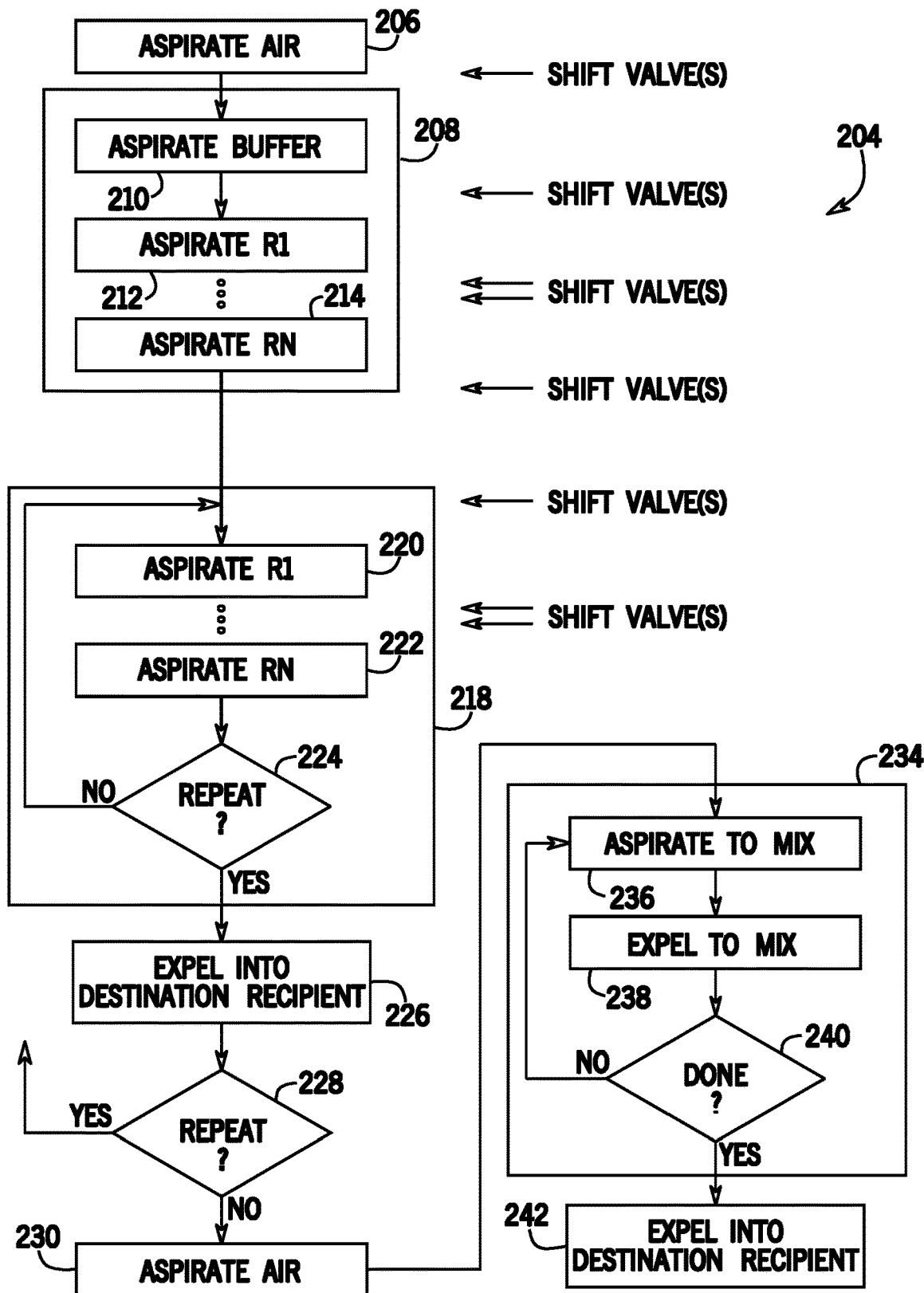
FIG. 11 is a flow chart illustrating example logic for aspirating and mixing reagents and a sample template.

FIG. 10 is a graphical representation of example cycles in aspirating, mixing and ejecting reagents and a sample template, while FIG. 11 is a flow chart illustrating example logic for aspirating and mixing reagents and a sample template. In FIG. 10, the aspiration, mixing, and ejection cycle is designated by reference numeral 180, with pressures applied by the pump indicated by axis 182 and times of the cycle by axis 184. Negative pressures indicate aspiration of one or more of the reagents, while positive pressures indicate ejection. The process may be considered to include a "transfer" sequence 186, followed by a "mixing" sequence 196, as discussed below.

Following the flow chart of FIG. 11, the control logic 204 may begin with aspirating air at 206 to remove existing liquid from flow paths through which previous mixtures of reagents may have been routed. For example, any leftover liquid remaining in the flow path 142, which links the reagent selector valve 66 with the destination recipient 136, may be aspirated with air (i.e., such that the liquid is replaced with air) so that any new mixture of reagents that is subsequently delivered to the destination recipient via the flow path 142 is not coming led with the leftover liquid. The transfer sequence may then begin with a priming sequence as indicated by reference 208 in FIG. 11. This priming sequence is indicated by the series of negative pressure or aspiration events collectively indicated by reference 188 in FIG. 10. In general, these events allow for drawing the reagents initially into the system. In somewhat greater detail, returning to FIG. 11, a buffer may be aspirated as indicated at 210. This buffer may comprise a liquid selected so as to be non-reactive or relatively inert with respect to the reagents and may be used as an incompressible working fluid that extends, at least in part, between the pump and the reagents to allow for more precise metering of the reagents into the mixing volume in the following steps, if desired. The first reagent may then be aspirated in a priming event as indicated at 212 in FIG. 11, followed by aspiration of any number of other reagents, through the aspiration of the final reagent at 214. In a presently contemplated implementation, for example, three such reagents are aspirated in the priming sequence.

In the logic illustrated in FIG. 11, the reagents to be mixed are then aspirated in a transfer sequence 218. The transfer sequence continues with aspiration of the first reagent as indicated at 220, followed by aspiration, one-by-one, of each of the additional reagents until the final reagent is aspirated as indicated at 222. As before, in a presently contemplated implementation three reagents are aspirated in this sequence. As noted above, in a presently contemplated implementation a number of sets of the reagents are aspirated in relatively small quantities to create a sequence of the reagents, and thereby to promote pre-mixing. Thus, at 224 the logic may determine whether all sets of the reagents have been aspirated, and if not, return to 220 to continue aspirating additional sets. It may also be noted that in the presently contemplated implementation all sets contain all reagents selected for mixing, although this need not be the case. Moreover, different volumes or quantities of reagents could be aspirated in the various sets. Once all of the reagents have an aspirated, control may advance beyond the transfer sequence. The transfer sequence is illustrated by the negative pressure events collectively indicated by reference numeral 190 in FIG. 10.

As shown in FIG. 11, and as will be clear from the separate negative (and positive) pressure events of FIG. 10, each successive aspiration (or ejection) of reagents or pre-mixed reagents involves controlling one or more of the valves described above, as well as the pump. That is, to aspirate the individual reagents, the reagent selector valve will be shifted to direct negative pressure to the sipper for the corresponding recipient of the selected reagent. The pump will similarly be commanded to draw the reagent (or air or buffer or template), and to express the aspirated fluids in accordance with the prescribed protocol. This mixing protocol will be predetermined and stored in the memory circuitry described above and carried out in an automated or semi-automated fashion based upon the sequencing operation, also defined in the memory circuitry. These protocols are executed by the processing and control circuitry which, through appropriate interface circuitry commands operation of the valves and pump.

Once all of the reagents have been aspirated, the aspirated fluids may be ejected into the destination recipient as indicated at 226 in FIG. 11. As noted above, in the presently contemplated implementation, this is done through the nozzle sipper where mixing begins by virtue of the increased velocity of the reagents through the nozzle and the resulting vorticity in the destination recipient. This ejection into the destination recipient is indicated by the positive pressure event 192 in FIG. 10. In certain implementations, aspiration may be further performed as indicated at reference 228 in FIG. 11. Thereafter, the aspirated reagents may be ejected into the destination recipient. This sequence may be followed by aspiration of air as indicated by reference numeral 230 in FIG. 11 and the negative pressure event 194 in FIG. 10 (e.g., to remove as much liquid as possible from the bypass line, mixing channel, template channel, and sipper). It may also be noted that in some implementations, the nozzle sipper, or the recipient, or both may be moved with respect to the other (e.g., vertically) during aspiration and ejection to further help mix striated samples and reagents.

Following aspiration and partial pre-mixing in the mixing volume or channel by the operations described above, mixing is performed by repeatedly moving the reagents in the channel, and between the channel and the destination recipient through the nozzle sipper. For this, a series of mixing cycles is implemented in a mixing sequence 234. In this sequence, the combined reagents and template are aspirated at 236 and ejected back into the destination recipient at 238. The logic may repeatedly determine whether all of these desired mixing cycles have been performed at 240, and continue until all such cycles are complete. In the graphical illustration of FIG. 10, the cycles are collectively indicated by reference 198. As may be seen, each involves a relatively short negative pressure event followed by a relatively short positive pressure event. These events effectively aspirate the combined reagents and template into the mixing volume or channel through the nozzle sipper, and return the progressively mixed reagents and template to the destination recipient through the nozzle. While any desired volume may be displaced in this process, in a presently contemplated implementation, about 2,000 µL are aspirated from and ejected into the destination recipient in each mixing cycle, although other implementations may dispense about 500 µL or 1500 µL, depending on the size of the flow cells that are used. At the end of the mixing process, the mixed reagents and template may be returned to the destination recipient for proceeding with the sequencing operation.

It may be noted that in a present implementation, the nozzle sipper effectively increases the velocity of the reagents (and mixed reagents) as they are mixed during aspiration and ejection. This increase in velocity increases the kinetic energy to aid in mixing. For example, in a presently contemplated implementation, the nozzle accelerates the mixture to least about 1600 mm/s at a flow rate of at least about 5,000 µL/min.

The use, if any, of ordinal indicators, e.g., (a), (b), (c) . . . or the like, in this disclosure and claims is to be understood as not conveying any particular order or sequence, except to the extent that such an order or sequence is explicitly indicated. For example, if there are three steps labeled (i), (ii), and (iii), it is to be understood that these steps may be performed in any order (or even concurrently, if not otherwise contraindicated) unless indicated otherwise. For example, if step (ii) involves the handling of an element that is created in step (i), then step (ii) may be viewed as happening at some point after step (i). Similarly, if step (i)

involves the handling of an element that is created in step (ii), the reverse is to be understood.

It is also to be understood that the use of "to," e.g., "a valve to switch between two flow paths," may be replaceable with language such as "configured to," e.g., "a valve configured to switch between two flow paths", or the like.

Terms such as "about," "approximately," "substantially," "nominal," or the like, when used in reference to quantities or similar quantifiable properties, are to be understood to be inclusive of values within ±10% of the values specified, unless otherwise indicated.

In addition to the implementations listed in this disclosure, the following additional implementations are to be understood to be within the scope of this disclosure:

Implementation 1: A system including: a flow cell to support analytes of interest in an analysis system; a fluidic system to aspirate reagents, to mix the reagents, and to eject the mixed reagents into a destination recipient; and a nozzle sipper in fluid communication with the fluidic system, the nozzle sipper including an elongated body having a central lumen extending between ends thereof and a nozzle insert disposed in a distal end though which the nozzle sipper aspirates reagents from the recipient and ejects mixed reagents back into the destination recipient.

Implementation 2: The system of implementation 1, in which the nozzle and lumen are dimensioned to promote vorticity mixing in the lumen when the reagents are aspirated into the sipper through the nozzle insert.

Implementation 3: The system of implementation 1, in which the lumen has a nominal inner diameter of about 0.5 mm and the nozzle insert has a nominal inner diameter of about 0.25 mm.

4: The system of implementation 1, in which the distal end of the nozzle sipper has a wedged shape with an apex that is offset with respect to a central axis of the nozzle sipper.

Implementation 5: The system of implementation 4, in which the nozzle insert has a distal end that is shape-compliant with the wedged shape of the distal end of the nozzle sipper.

Implementation 6: The system of implementation 4, in which the wedged shape includes four facets meeting in the apex.

Implementation 7: The system of implementation 1, in which nozzle sipper has a length to extend to a nominal distance 2 mm from a bottom surface of the recipient.

Implementation 8: The system of implementation 1, including a plurality of other sippers for aspirating respective reagents, in which the other sippers do not include nozzle inserts.

Implementation 9: The system of implementation 1, in which the sipper nozzle accelerates the mixed recipients to at least about 1600 mm/s at a flow rate of at least about 5,000 µL/min.

Implementation 10: A system including: a flow cell to support analytes of interest in an analysis system; a plurality of reagents disposed in respective recipients; a fluidic system to aspirate reagents, to mix the reagents, and to eject the mixed reagents into a destination recipient; a nozzle sipper in fluid communication with the fluidic system, the nozzle sipper including an elongated body having a central lumen extending between ends thereof and a nozzle at a distal end; and control circuitry operatively coupled to the fluidic system to command the fluidic system to aspirate a plurality of reagents one-by-one, to eject the plurality of reagents into the destination recipient through the nozzle, to aspirate the plurality of reagents from the destination recipient through the nozzle for mixing, and to eject the mixed reagents back into the recipient through the nozzle.

Implementation 11: The system of implementation 10, in which the nozzle includes an insert in the distal end of the nozzle sipper.

Implementation 12: The system of implementation 10, in which the destination recipient includes an analyte to be sequenced.

Implementation 13: The system of implementation 10, in which the lumen has a nominal inner diameter of 0.5 mm and the nozzle has a nominal inner diameter of 0.25 mm.

Implementation 14: The system of implementation 10, in which the distal end of the nozzle sipper has a wedged shape with an apex that is offset with respect to a central axis of the nozzle sipper.

Implementation 15: The system of implementation 14, in which the nozzle has a distal end that is shape-compliant with the wedged shape of the distal end of the nozzle sipper.

Implementation 16: A method including: actuating a pump to aspirate a plurality of reagents from a destination recipient containing an analyte to be analyzed; aspirating the plurality of reagents through a nozzle sipper in fluid communication with the pump to mix the plurality of reagents, the nozzle sipper including an elongated body having a central lumen extending between ends thereof and a nozzle at a distal end; and actuating the pump to eject the mixed reagents into the destination recipient.

Implementation 17: The method of implementation 16, in which the nozzle and lumen are dimensioned to promote vorticity mixing in the lumen when the reagents are aspirated into the sipper through the nozzle.

Implementation 18: The method of implementation 16, in which the lumen has a nominal inner diameter of 0.5 mm and the nozzle includes an insert that has a nominal inner diameter of 0.25 mm.

Implementation 19: The method of implementation 16, in which the distal end of the nozzle sipper has a wedged shape with an apex that is offset with respect to a central axis of the nozzle sipper.

Implementation 20: The method of implementation 16, in which the reagents include at least three reagents of different specific gravities.

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

What is claimed is:

1. A system comprising:
  a flow cell flow path configured to be fluidically connected with a flow cell configured to support analytes of interest in an analysis system;
  a fluidic system comprising a plurality of reagent flow paths, a further flow path, a mixing channel, and a selector valve, wherein:
    each of the plurality of reagent flow paths has a first end configured to be fluidically connected with a different reagent recipient of a plurality of reagent recipients and a second end fluidically connected with the selector valve, the further flow path has a first end configured to be fluidically connected with a destination recipient and a second end fluidically connected with the selector valve, the mixing channel has a first end fluidically connected to the selector valve, and the fluidic system is configured to:
aspirate reagents from the plurality of reagent recipients into the mixing channel via the selector valve,
eject the aspirated reagents from the mixing channel into the destination recipient via the selector valve and the further flow path, and
deliver the reagents from the destination recipient to the flow cell flow path; and a nozzle sipper fluidically connected with the further flow path, the nozzle sipper comprising an elongated body having a central lumen extending between a proximal end of the elongated body and a distal end of the elongated body and a nozzle insert disposed in the distal end of the elongated body, wherein the fluidic system is configured to both aspirate the mixed reagents from the destination recipient and eject mixed reagents back into the destination recipient via the nozzle insert.

2. The system of claim 1, wherein the nozzle insert and elongated body are dimensioned to promote vorticity mixing in the destination recipient when the reagents are expelled from the nozzle sipper through the nozzle insert and into the destination recipient.

3. The system of claim 1, wherein the central lumen has a nominal inner diameter of about 0.5 mm and narrows to about 0.25 mm at the nozzle insert.

4. The system of claim 1, wherein the distal end of the nozzle sipper has a wedged shape with facets meeting at an apex that is offset with respect to a central axis of the nozzle sipper.

5. The system of claim 4, wherein the nozzle insert has a distal end that is shape-compliant with the wedged shape of the distal end of the nozzle sipper.

6. The system of claim 4, wherein the wedged shape comprises four facets meeting at the apex.

7. The system of claim 1, wherein the nozzle sipper is configured to extend to a nominal distance of 2 mm from a bottom surface of the destination recipient when the nozzle sipper is fluidically connected with the destination recipient.

8. The system of claim 1, comprising a plurality of other sippers configured for aspirating respective reagents from the plurality of reagent recipients, wherein the other sippers do not have nozzle inserts.

9. The system of claim 1, wherein the nozzle sipper is sized so as to accelerate fluid that is flowed through the nozzle sipper at a flow rate of at least about 5,000 μL/min to a flow velocity of at least about 1600 mm/s.

10. A system comprising:
a flow cell configured to support analytes of interest in an analysis system;
a fluidic system comprising a plurality of reagent flow paths, a further flow path, a mixing channel, and a selector valve, wherein:
each of the plurality of reagent flow paths has a first end configured to be fluidically connected with a different reagent recipient of a plurality of reagent recipients and a second end fluidically connected with the selector valve,
the further flow path has a first end configured to be fluidically connected with a destination recipient and a second end fluidically connected with the selector valve,
the mixing channel has a first end fluidically connected to the selector valve;
a nozzle sipper fluidically connected with the further flow path, the nozzle sipper comprising an elongated body having a proximal end and a distal end and a nozzle located at the distal end of the elongated body, wherein the nozzle sipper has a central lumen extending from the proximal end of the elongated body to the nozzle, wherein the nozzle reduces a nominal interior diameter of the central lumen; and
control circuitry operatively coupled to the fluidic system, the control circuity comprising one or more processors and one or more memory devices storing computer-executable instructions that, when executed by the one or more processors, cause the fluidic system to:
aspirate a set of the reagents one-by-one from the plurality of reagent recipients into the mixing channel via the selector valve,
eject the reagents in the set of reagents from the mixing channel into the destination recipient via the selector valve and the further flow path through the nozzle,
aspirate the set of reagents from the destination recipient through the nozzle for mixing, and
eject the set of mixed reagents back into the destination recipient through the nozzle.

11. The system of claim 10, wherein the nozzle comprises an insert inserted into the distal end of the elongated body.

12. The system of claim 10, wherein the system further comprises the destination recipient, and wherein the destination recipient contains an analyte to be sequenced.

13. The system of claim 10, wherein the central lumen has a nominal inner diameter of 0.5 mm and narrows to about 0.25 mm at the nozzle.

14. The system of claim 10, wherein the distal end of the nozzle sipper has a wedged shape with facets meeting at an apex that is offset with respect to a central axis of the nozzle sipper.

15. The system of claim 14, wherein the nozzle has a distal end that is shape-compliant with the wedged shape of the distal end of the nozzle sipper.

* * * * *